United States Patent [19]

Morita et al.

[11] Patent Number: 4,735,987
[45] Date of Patent: Apr. 5, 1988

[54] METHOD FOR MANUFACTURE OF HIGH-EXPANSION TYPE ABSORBENT POLYMER

[75] Inventors: Yasuhiro Morita, Osaka; Takanori Iwamoto, Osaka; Hiroyuki Kataoka, Osaka; Taiji Kambayashi, Yamatotakada; Shigeaki Matsumoto, Yamatokoriyama; Chuzo Kato, Tokyo, all of Japan

[73] Assignee: Osaka Yuki Kagaku Kogyo Kabushiki Kaisha, Osaka, Japan

[21] Appl. No.: 880,447

[22] Filed: Jun. 30, 1986

[30] Foreign Application Priority Data

Mar. 25, 1986 [JP] Japan .................................. 61-64773
Apr. 26, 1986 [JP] Japan .................................. 61-95884
Apr. 26, 1986 [JP] Japan .................................. 61-95885

[51] Int. Cl.$^4$ .......................... C08F 2/00; C08K 3/34
[52] U.S. Cl. ................................. 524/436; 524/445; 524/447; 524/451; 524/424; 524/437; 528/501; 526/80
[58] Field of Search ............... 524/424, 445, 451, 447, 524/436; 526/80; 528/501

[56] References Cited

U.S. PATENT DOCUMENTS

| | | | |
|---|---|---|---|
| 4,056,502 | 11/1977 | Gross | 525/375 |
| 4,460,642 | 7/1984 | Errede et al. | 128/156 |
| 4,587,308 | 5/1986 | Makita et al. | 525/374 |

*Primary Examiner*—Joseph L. Schofer
*Assistant Examiner*—Peter F. Kulkosky
*Attorney, Agent, or Firm*—Armstrong, Nikaido, Marmelstein & Kubovcik

[57] ABSTRACT

This invention provides a method for the manufacture of a high-expansion type absorbent polymer by first causing an absorbent polymer which is obtained by polymerization of a monomer and is possessed of an alkali salt of acrylic acid as a component of polymer to be cross-linked at the time of azeotropic dehydration thereof with a cross-linking agent possessing two or more functional groups in the presence of an inorganic salt and subsequently drying the cross-linked polymer. By the method of this invention, there can be obtained a high-expansion type absorbent material which absorbs water quickly and forms a gel not viscid but permeable to gas. This absorbent material is highly advantageously used as absorbent for sanitary materials free from leaking water and as a water-retaining agent for agricultural applications hardly causing rotten plant roots.

8 Claims, 1 Drawing Sheet

METHOD FOR MANUFACTURE OF HIGH-EXPANSION TYPE ABSORBENT POLYMER

BACKGROUND OF THE INVENTION (1) Field of the Invention

This invention relates to a method for the manufacture of a high-expansion type absorbent polymer. The polymer manufactured by the present invention is of a high-expansion type and enjoys a high permeability to gas. The gel which the polymer forms with absorbed water has no viscidity. Thus, the polymer is used as water-retaining materials for agricultural and horticultural soils and as sanitary materials (such as paper diaper and sanitary napkin).

(2) Description of the Prior Art

Absorbent polymers are advantageous synthetic polymers which are used as physiological articles, sanitary materials such as paper diaper, and water-retaining materials for agricultural and horticultural applications, which are also used in various applications such as solidification of sludge and dehydration of oils, and for which new uses are being developed. Concrete examples of such polymers which have been introduced to the art include (1) the hydrolyzate of a starch-acrylonitrile graft polymer (Japanese Patent Publication No. 46199/1978 and Japanese Patent Application Laid-open No. 4820/1980), (2) a modified cellulose (Japanese Patent Application Laid-open No. 80376/1975), (3) polysodium acrylate obtained by the reversed-phase suspension method (Japanese Patent Publication No. 30710/1979 and Japanese Patent Application Laid-open No. 26909/1981), (4) polysodium acrylate obtained by the aqueous solution polymerization method (adiabatic polymerization and thin-film polymerization) (Japanese Patent Application Laid-open No. 133413/1980), (5) a cross-linked water-soluble macromolecular substance (Japanese Patent Publication No. 23462/1968), and (6) a starch-sodium acrylate graft polymer (Japanese Patent Publication No. 46199/1978).

The methods for the manufacture of the absorbent polymers enumerated above, however, have entailed the following problems.

(1) Insufficient capacity for absorption of water or slow speed of absorption of water in spite of high capacity for water absorption. Or inferior dispersibility in water.

(2) The gels which the absorbent polymers form with absorbed water are so viscid that the polymers, when used as sanitary materials, have the possibility of exerting adverse effects on the user's skin.

(3) An aggregate which polymer particles form when they are swelled with absorbed water has poor permeability to gas. The polymer, when used as a water-retaining material for soil, therefore, has the possibility of rotting the roots in the soil.

SUMMARY OF THE INVENTION

The inventors have continued a diligent study for the purpose of overcoming the drawbacks suffered by the conventional absorbent polymers. They have consequently perfected a method for the manufacture of a high-expansion type polymer which quickly swells with absorbed water and consequently forms a gel not viscid but permeable to gas.

In accordance with this invention, there is provided a method for the manufacture of a high-expansion type absorbent polymer, characterized by causing an absorbent polymer which results from the polymerization of a monomer and possesses an alkali salt of acrylic acid as a component of polymer to be cross-linked, during azeotropic dehydration thereof, with a cross-linking agent possessing two or more functional groups in the presence of an inorganic substance and then drying the cross-linked absorbent polymer.

DETAILED DESCRIPTION OF THE INVENTION

Figure 1:
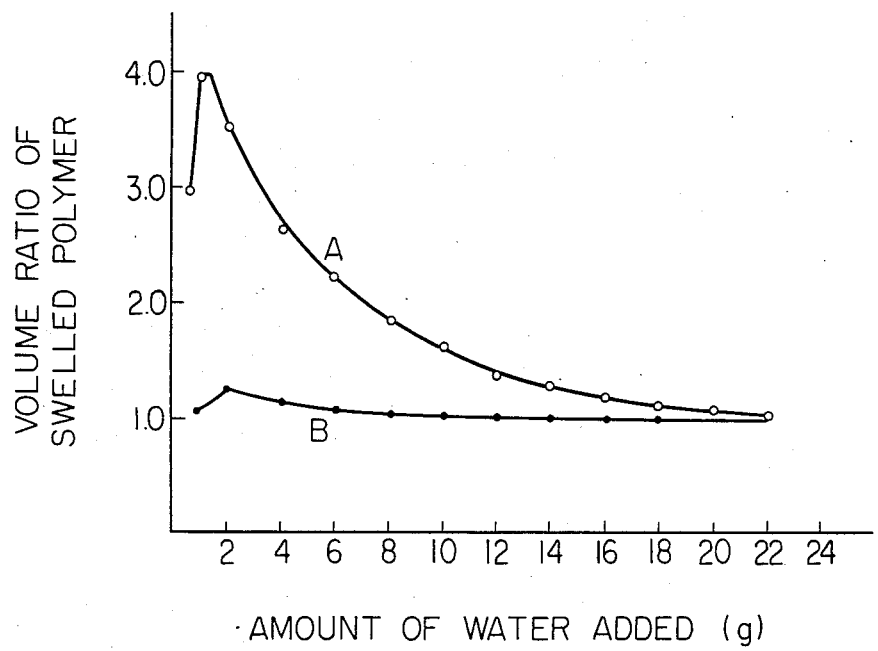
FIG. 1 is a graph showing the relation between the amount of ion-exchange water and the volume ratio, $V/V_o$ (wherein $V_o$ stands for the volume of water added and V for the volume of swelled polymer), of the swelled polymer obtained when the ion-exchange water was added to 0.2 g of dry polymer. In the graph, the curve A represents the test results of a dry polymer obtained in Example 1 and the curve B the test results of a commercially available polymer.

In the method of the present invention, the polymer is desired to be obtained by allowing an aqueous solution containing not less than 40% by weight of a vinyl monomer possessing a carboxyl group to be dispersed and suspended in an aliphatic hydrocarbon type solvent in the presence of a dispersant an starting the monomer polymerizing by the use of a water-soluble radical polymerization initiator.

As absorbent polymers containing alkali salts of acrylic acid as components of polymer and used for this invention, not only alkali salts of homopolymers of acrylic acid but also alkali salts of acrylic acid copolymers obtained by copolymerizing acrylic acid or alkali salts of acrylic acid with monomers copolymerizable therewith are embraced.

As monomers copolymerizable with acrylic acid or alkali salts of acrylic acid, there may be cited acrylic esters such as methyl acrylate and ethyl acrylate; methacrylic esters such as methyl methacrylate and ethyl methacrylate; hydroxyalkyl acrylates such as hydroxyethyl acrylate; hydroxyalkyl methacrylates such as hydroxyethyl methacrylate; and vinyl aromatic monomers such as styrene, α-methylstyrene, and p-methylstyrene. The copolymer is desired to contain not less than 75 mol % of an alkali salt of acrylic acid.

As means of obtaining a high-expansion type polymer containing a carboxyl group, the W/O suspension polymerization proves desirable from the viewpoint of workability, for example, because the polymer to be formed is subsequently dried by azeotropic dehydration. As surfactants usable in the W/O suspension polymerization, there can be cited sorbitan fatty acid esters such as sorbitan monostearate, sorbitan distearate. and sorbitan monolaurate, cellulose ethers such as ethyl cellulose and benzyl cellulose, and macromolecular dispersants such as polyethylene maleate and polybutadiene maleate. One member or a mixture of two or more members selected from the group cited above may be used. As hydrophobic solvents usable for the W/O suspension polymerization, there can be cited aliphatic hydrocarbons such as n-hexane, heptane, and octane, alicyclic hydrocarbons such as cyclohexane, methyl cyclohexane, and Decalin, aromatic hydrocarbons such as benzene, toluene, and xylene, and halogenated hydrocarbons such as chlorobenzene and dichlorobenzene.

The requirement particularly important for the method of this invention is that the cross-linking reaction should be carried out during azeotropic dehydration in the presence of an inorganic substance. The inorganic substance to be effectively used in this invention is required to be capable of enhancing the permeability to gas of the polymer particles aggregated as swelled with absorbed water, improving the water-retaining capacity of the polymer, and further permitting high expansion of polymer particles. Concrete examples of inorganic substance satisfying the requirement are as follows.

(1) Binary metal hydroxides such as natural and synthetic hydrotalcites which have an anion-exchange capacity.

(2) Natural and synthetic lamellar viscid minerals possessing a cation-exchange capacity. Particularly binary metal hydroxides such as expansion lattice type montmorillonite of lamellar construction which have a cation-exchange capacity bring about advantageous results. The activated clay obtained by treating montmorillonite with an acid similarly produces desirable results.

(3) Talc, pyrophillite, and kaolinite having a lamellar construction.

The reason for the rapidity with which the high-expansion type absorbent polymer obtained by this invention swells with absorbed water is not clear. But, (1) the fact that the polymer resulting from the treatments of polymerization and drying shows no swelling property and exhibits different data of IR and X-ray diffraction when it is simply mixed with an inorganic substance and (2) the fact that the polymer fails to swell during the azeotropic dehydration in the absence of either the inorganic substance or the cross-linking agent admit of the following inference.

The polymer is a slurry state obtained by the polymerization of an alkali salt of acrylic acid, the inorganic substance, and the cross-linking agent jointly form an entirely new composite in which the components alternate with one another on the molecular order. When the composite absorbs water, therefore, it is enabled to exhibit a swelling property by the ionic repulsion between the carboxylic groups in the composite.

Although the amount of the inorganic substance to be added is variable with the kind of the inorganic substance and the kind of the polymer, generally the proper amount thereof falls in the range of 0.5 to 30% by weight, preferably 5 to 20% by weight, based on the monomer. If the amount of the inorganic substance to be added is less than 0.5% by weight, the polymer does not show the high expansion property. If it exceeds 30% by weight, the polymer particles during the addition of the inorganic substance tends to aggregate and induce the phenomenon of blocking.

The cross-linking agent to be used effectively in the present invention can be any compound which has two or more functional groups capable of reacting with carboxyl groups (or carboxylate groups). As cross-linking agents satisfying this requirement, there can be cited polyglycidyl ethers such as ethylene glycol diglycidyl ether, polyethylene glycol diglycidyl ether, and glycerin triglycidyl ether; haloepoxy compounds such as epichlorohydrin and α-methyl chlorohydrin; and polyaldehydes such as glutaraldehyde and glyoxal.

The amount of the cross-linking agent to be added is variable with the kind of the cross-linking agent and the kind of the polymer. Generally, however, the proper amount of the cross-linking agent falls in the range of 0.05 to 2% by weight, preferably 0.2 to 1.0% by weight, based on the monomer. If the amount of the cross-linking agent is less than 0.05% by weight, the polymer undergoes the phenomenon of conglomeration and fails to acquire the high expansion property. If this amount exceeds 2% by weight, the cross-linking density is higher and the capacity for absorption of water is notably lower than expected.

The high-expansion type absorbent polymer obtained by the present invention swells to the maximum of four times the original volume with absorbed water. This high-expansion type polymer is not obtained by adding either the inorganic substance alone or the cross-linking agent alone. This invention does not contemplate selectively adding the inorganic substance or the cross-linking agent.

By the use of the method of this invention, it is made possible to obtain a high-expansion type absorbent material which has a high capacity for absorption of water, absorbs water rapidly, and forms a gel not viscid but permeable to gas. This material has no possibility of adversely affecting the user's skin through leakage of absorbed water or rotting the roots in the soil. Thus, it is used with immense advantage as absorbents in sanitary materials and as a water-retaining agent in agricultural and horitcultural applications.

Now, the method of this invention will be described more specifically below with reference to working examples. The numerical values of the capacity for water absorption and the volume ratio indicated in the following working examples and the comparative experiments were obtained by the following procedures.

The capacity for absorption of ion-exchange water was determined by dispersing 0.5 g of dry polymer in 1 liter of ion-exchange water, allowing the dispersed water to stand at rest overnight, filtering the resulting dispersion through a metal gauze of 60 meshes, measuring the weight (W) of the swelled polymer stopped on the metal gauze, and dividing this weight by the initial weight (Wo) of dry polymer. Thus, the capacity for absorption of ion-exchange water (g/g) represents W/Wo.

The capacity for absorption of physiological salt solution was determined by dispersing 0.2 g of dry polymer in 60 g of 0.9% salt water, allowing the resulting dispersion to stand at rest for 20 minutes, filtering the dispersion through a metal gauze of 100 meshes, measuring the weight (W) of swelled polymer stopped on the metal gauze, and dividing this weight by the initial weight (Wo) of dry polymer. Thus, the capacity for absorption of physiological salt solution (g/g) represents W/Wo.

The volume ratio was determined by placing 0.2 g of dry polymer (the fraction stopped on a 42-mesh sieve and passed through a 16-mesh sieve) in a Nessler tube, measuring the volume (V) of swelled polymer consequently obtained, and dividing this volume with the volume (Vo) of water added. Thus, the volume ratio ($cm^3/cm^3$) represents V/Vo.

The volume ratios indicated in Examples 2–16 and Comparative Experiments 1–3 each represents the value of swelled polymer obtained by placing 0.2 g of the aforementioned dry polymer in a Nessler tube and adding thereto 2.0 g of ion-exchange water.

EXAMPLE 1

In a separable flask having an inner volume of 1 liter and provided with a stirrer, a reflux condenser, a dropping funnel, and a nitrogen gas inlet tube, 360.7 g of n-hexane and 4.32 g of sorbitan mono-laurate were heated to 50° C. for dissolution. At room temperature, the resulting solution was added with an aqueous solution obtained by dissolving 0.24 g of potassium persulfate in 10 g of water.

Separately, in an Erlenmeyer flask, 72.0 g of acrylic acid was partially neutralized with 32.2 g of sodium hydroxide dissolved in 93.6 g of water and the monomer concentration in the aqueous monomer solution was adjusted to 43%. This aqueous monomer solution was added dropwise into the aforementioned separable flask over a period of one hour, with the solution therein kept bubbled with nitrogen gas, to induce polymerization of the monomer. The resulting mixture was refluxed for one hour, admixed with 0.1 g of an aqueous 30% hydrogen peroxide solution, and refluxed again for two hours.

Subsequently, the refluxed mixture was admixed with 8.85 g of synthetic hydrotalcite ($Mg_6Al_2(OH)_{16}CO_3 4-H_2O$, a product of Kyowa Chemical and marketed under trademark designation of "Kyoward 500") and 0.73 g of ethylene glycol diglycidyl ether and dried by azeotropic dehydration. There was consequently obtained a while powdery polymer.

This dry polymer was found to have an absorption capacity of 210 (g/g) for ion-exchange water an absorption capacity of 40 (g/g) for physiological salt water, and a volume ratio of 3.5 ($cm^3/cm^3$) (with 2.0 g of added water).

By adding ion-exchange water to 0.2 g of the dry polymer (the fraction passed through a 16-mesh sieve), the relation between the amount of the ion-exchange water so added and the volume ratio, V/Vo, of the swelled polymer was studied. The results were shown by the curve A in FIG. 1. It is noted from the curve that the polymer showed a notably larger volumnious expansion than the volume corresponding to the amount of water added. For comparison, the same test was conducted on 0.2 g of a commercially available sodium acrylate type absorbent polymer (product of Kao Co., Ltd. marketed under trademark designation of "Poise S-20"). The results were shown by the curve B in FIG. 1. It is noted from the curve that the polymer showed a small voluminous expansion.

EXAMPLE 2

A white powdery polymer was obtained by carring out polymerization and drying in accordance with the procedure of Example 1, except that 4.32 g of sorbitan monostearate was used in the place of sorbitan monolaurate. The dry polymer consequently obtained was found to have an absorption capacity of 145 (g/g) for ion-exchange water, an absorption capacity of 31 (g/g) for physiological salt water, and a volume ratio of 3.0 ($cm^3/cm^3$).

EXAMPLE 3

A white powdery polymer was obtained by carrying out polymerization and drying in accordance with the procedure of Example 1, except that 4.32 g of sorbitan distearate was used in the place of sorbitan monolaurate. This dry polymer was found to have an absorption capacity of 120 (g/g) for ion-exchange water, an absorption capacity of 28 (g/g) for physiological salt water, and a volume ratio of 3.3 ($cm^3/cm^3$).

EXAMPLE 4

In a polymerization carried out by following the procedure of Example 1, 8.85 g of a varying inorganic substance indicated in Table 1 and 0.73 g of ethylene glycol glycidyl ether were added while the produced polymer was dried by azeotropic dehydration. Consequently, there was obtained a white powdery polymer.

TABLE 1

| No. | Inorganic substance | Absorption capacity (g/g) | | Volume ratio ($cm^3/cm^3$) |
| --- | --- | --- | --- | --- |
| | | Ion-exchange water | Physiological salt water | |
| 1 | Kyoward 400 ($Al_2O_3 \cdot Na_2O \cdot 2CO_3 \cdot xH_2O$) | 190 | 32 | 2.8 |
| 2 | Kyoward 600 ($2MgO \cdot 6SiO_2 \cdot xH_2O$) | 150 | 33 | 3.2 |
| 3 | Kyoward 700 ($Al_2O_3 \cdot 9SiO_2 \cdot xH_2O$) | 160 | 35 | 3.1 |

EXAMPLE 5

In a polymerization carried out by following the procedure of Example 1, varying amounts of an inorganic substance and ethylene glycol diglycidyl ether indicated in Table 2 were added while the produced polymer was dried by azeotropic dehydration. Consequently there was obtained a white powdery polymer.

TABLE 2

| No. | Kyoward 500 (g) | Ethylene glycol diglycidyl ether (g) | Absorption capacity (g/g) | | Volume ratio ($cm^3/cm^3$) |
| --- | --- | --- | --- | --- | --- |
| | | | Ion-exchange water | Physiological salt water | |
| 1 | 4.43 | 0.73 | 220 | 34 | 3.0 |
| 2 | 17.7 | 0.73 | 180 | 34 | 2.7 |
| 3 | 4.43 | 0.37 | 260 | 38 | 2.5 |
| 4 | 17.7 | 0.37 | 200 | 40 | 2.8 |

COMPARATIVE EXPERIMENT 1

In a polymerization carried out by following the procedure of Example 1, 8.85 g of Kyoward 500 alone was added while the polymer was dried by azeotropic dehydration. Consequently, there was obtained a white powdery polymer. The polymer was found to have an absorption capacity of 80 (g/g) for ion-exchange water, an absorption capacity of 47 (g/g) for physiological salt water, and a volume ratio of 1.3 ($cm^3/cm^3$).

COMPARATIVE EXPERIMENT 2

In a polymerization carried out by following the procedure of Example 1, 0.73 g of ethylene glycol diglycidyl ether alone was added while the produced polymer was dried by azeotropic dehydration. Consequently there was obtained a white powdery polymer. This polymer was found to have an absorption capacity of 120 (g/g) for ion-exchange water, an absorption capacity of 31 (g/g) for physiological salt water, and a volume ratio of 1.5 ($cm^3/cm^3$).

COMPARATIVE EXPERIMENT 3

When 100 parts of the polymer of Comparative Experiment 1 was thoroughly mixed with 10 parts of Kyoward 500, the produced mixture was found to have an absorption capacity of 120 (g/g) for ion-exchange water, an absorption capacity of 35 (g/g) for physiological salt water, and a volume ratio of 1.5 ($cm^3/cm^3$).

EXAMPLE 6

In a separable flask having an inner volume of 1 liter and provided with a stirrer, a reflux condenser, a dropping funnel, and a nitrogen gas inlet tube, 360.7 g of n-hexane and 4.32 g of sorbitan monolaurate were heated to 50° C. for dissolution. At room temperature, the resulting solution was admixed with an aqueous solution obtained by dissolving 0.24 g of potassium persulfate in 10 g of water.

Separately, in an Erlenmeyer flask, 72.0 g of acrylic acid was partially neutralized with 32.2 g of sodium hydroxide dissolved in 93.6 g of water. The monomer concentration in the aqueous monomer solution was adjusted to 43%. This aqueous monomer solution was added dropwise into the separable flask over a period of one hour, with the solution therein kept bubbled with nitrogen gas, to induce polymerization of the monomer. The resulting mixture was refluxed for one hour, admixed with 0.1 g of an aqueous 30% hydrogen peroxide solution, and again refluxed for two hours.

Subsequently, the refluxed mixture was admixed with 8.85 g of montmorillonite (produced in Hidarisawa of Yamagata Prefecture, Japan, and having a chemical composition of 57% of $SiO_2$, 0.01% of $TiO_2$, 21.9% of $Al_2O_3$, 1.92% of $Fe_2O_3$, 3.50% of MgO, 0.63% of CaO, 2.85% of $Na_2O$, 0.17% of $K_2O$, and 10.90% of $H_2O$) and 0.73 g of ethylene glycol diglycidyl ether and dried by azeotropic dehydration. Consequently, there was obtained a white powder polymer.

The dry polymer thus obtained was found to have an absorption capacity of 190 (g/g) for ion-exchange water, an absorption capacity of 35 (g/g) for physiological salt water, and a volume ratio of 3.0 ($cm^3/cm^3$) (with 2.0 g of added water).

EXAMPLE 7

A white powdery polymer was obtained by carrying out polymerization and drying in accordance with the procedure of Example 6, except that 4.32 g of sorbitan monostearate was used in the place of sorbitan monolaurate. The dry polymer thus obtained was found to have an absorption capacity of 150 (g/g) for ion exchange water, an absorption capacity of 33 (g/g) for physiological salt water, and a volume ratio of 2.8 ($cm^3/cm^3$).

EXAMPLE 8

A white powdery polymer was obtained by carrying out polymerization and drying in accordance with the procedure of Example 6, except that 4.32 g of sorbitan distearate was used in the place of sorbitan monolaurate. The dry polymer so obtained was found to have an absorption capacity of 110 (g/g) for ion exchange water, an absorptin capacity of 30 (g/g) for physiological salt solution, and a volume ratio of 2.6 ($cm^3/cm^3$).

EXAMPLE 9

In a polymerization carried out by following the procedure of Example 6, 8.85 g of a varying inorganic substance indicated in Table 3 and 0.73 g of ethylene glycoldiglycidyl ether were added while the produced polymer was dried by azeotropic dehydration. Consequently, there was obtained a white powdery polymer.

TABLE 3

| No. | Inorganic substance | Absorption capacity (g/g) | | Volume ratio ($cm^3/cm^3$) |
| --- | --- | --- | --- | --- |
| | | Ion-exchange water | Physiological salt water | |
| 1 | Montmorillonite (produced in Itoigawa of Niigata Prefecture) | 160 | 40 | 3.0 |
| 2 | Activated clay $V_1$ (product of Mizusawa Chemical) | 160 | 34 | 2.3 |
| 3 | Activated clay $V_2$ (product of Mizusawa Chemical) | 210 | 42 | 3.5 |

EXAMPLE 10

In a polymerization carried out by following the procedure of Example 6, varying amounts of an inorganic substance and ethylene glycol diglycidyl ether indicated in Table 4 were added while the produced polymer was dried by azeotropic dehydration. Consequently, a white powdery polymer was obtained.

TABLE 4

| No. | Montmorillonite (produced in Sazawa of Yamagata Prefecture) | Ethylene glycol diglycidyl ether (g) | Absorption capacity (g/g) | | Volume ratio ($cm^3/cm^3$) |
| --- | --- | --- | --- | --- | --- |
| | | | Ion-exchange water | Physiological salt water | |
| 1 | 4.43 | 0.73 | 180 | 38 | 2.9 |
| 2 | 17.7 | 0.73 | 200 | 36 | 3.0 |
| 3 | 4.43 | 0.37 | 230 | 42 | 2.4 |
| 4 | 17.7 | 0.37 | 210 | 35 | 2.6 |

EXAMPLE 11

In a separable flask having an inner volume of 1 liter and provided with a stirrer, a reflux condenser, a dropping funnel, and a nitrogen gas inlet tube, 360.7 g of n-hexane and 4.32 g of sorbitan monolaurate were heated to 50° C. for dissolution. At room temperature the resulting solution was admixed with an aqueous solution obtained by dissolving 0.24 g of potassium persulfate in 10 g of water.

Separately, in an Erlenmeyer flask, 72.0 g of acrylic acid was partially neutralized with 32.2 g of sodium hydroxide dissolved in 93.6 g of water and the monomer concentration in the aqueous monomer solution was adjusted to 43%. This aqueous monomer solution was added dropwise into the aforementioned separable flask over a period of one hour to induce polymerization of the monomer. The resulting mixture was refluxed for one hour, admixed with 0.1 g of an aqueous 30% hydrogen peroxide solution, and again refluxed for two hours.

Subsequently, the refluxed mixture was admixed with 8.85 g of talc (produced in Ogushi of Nagasaki Prefecture, Japan, and having a chemical composition of 62.53% of $SiO_2$, 1.05% of $Al_2O_3$, 1.34% of $Fe_2O_3$, 0.15% of CaO, 30.96% of MgO, 0.11% of $Na_2O$, 0.05% of $K_2O$, and 4.67% of $H_2O$) and 0.73 g of ethylene glycol diglycidyl ether and dried by azeotropic dehydration. Consequently, there was obtained a white powdery polymer.

The dry polymer so obtained was found to have an absorption capacity of 200 (g/g) for ion exchange water, an absorption capacity of 45 (g/g) for physiological salt water, and a volume ratio of 3.0 ($cm^3/cm^3$) (with 2.0 g of added water).

EXAMPLE 12

A white powdery polymer was obtained by carrying out polymerization and drying in accordance with the procedure of Example 11, except that 4.32 g of sorbitan monostearate was used in the place of sorbitan monolaurate. The dry monomer so produced was found to have an absorption capacity of 160 (g/g) for ion exchange water, an absorption capacity of 34 (g/g) for physiological salt solution, and a volume ratio of 2.9 ($cm^3/cm^3$).

EXAMPLE 13

A white powdery polymer was obtained by carrying out polymerization and drying in accordance with the procedure of Example 11, except that 4.32 g of sorbitan distearate was used in the place of sorbitan monolaurate. The dry polymer so obtained was found to have an absorption capacity of 120 (g/g) for ion exchange water, an absorption capacity of 31 (g/g) for physiological salt solution, and a volume ratio of 2.5 ($cm^3/cm^3$).

EXAMPLE 14

In a polymerization carried out by following the procedure of Example 11, 8.85 g of kaolinite as an inorganic substance (produced in Kawachi of Tochigi Prefecture, Japan, marketed under trademark designation of "Kanpaku Kaolin," and having a chemical composition of 45.75% of $SiO_2$, 39.78% of $Al_2O_3$, 0.63% of $Fe_2O_3$, 0.35% of CaO, 0.11% of MgO, 0.02% of $Na_2O$, and 14.05% of $H_2O$) and 0.73 g of ethylene glycol diglycidyl ether were added while the produced polymer was dried by azeotropic dehydration. Consequently, there was obtained a white powdery polymer.

The dry polymer so produced was found to have an absorption capacity of 180 (g/g) for ion exchange water, an absorption capacity of 41 (g/g) for physiological salt solution, and a volume ratio of 2.9 ($cm^3/cm^3$).

EXAMPLE 15

In a polymerization carried out by following the procedure of Example 11, 8.85 g of pyrophyllite as an inorganic substance (produced in Robin, N.C., U.S.A., and having a chemical composition of 77.54% of $SiO_2$, 16.65% of $Al_2O_3$, 0.41% of $Fe_2O_3$, 0.05% of MgO, 0.435 of CaO, 0.21% of $Na_2O$, 1.10% of $K_2O$, 0.17% of $TiO_2$, and 2.95% of $H_2O$) 0.73 g of ethylene glycol diglycidyl ether were added while theproduced polymer was dried by azeotropic dehydration. Consequently, there was obtained a white powdery polymer.

The dry polymer so obtained was found to have an absorption capacity of 170 (g/g) for ion exchange water, an absorption capacity of 38 (g/g) for physiological salt solution, and a volume ratio of 2.6 ($cm^3/cm^3$).

EXAMPLE 16

In a polymerization carried out by following the procedure of Example 11, varying amounts of an inorganic substance and ethylene glycol diglycidyl ether indicated in Table 5 were added while the produced polymer was dried by azeotropic dehydration. Consequently, there was obtained a white powdery polymer.

TABLE 5

| No. | Talc (g) | Ethylene glycol diglycidyl ether (g) | Absorption capacity (g/g) | | Volume ratio ($cm^3/cm^3$) |
| --- | --- | --- | --- | --- | --- |
| | | | Ion-exchange water | Physiological salt water | |
| 1 | 4.43 | 0.73 | 180 | 38 | 2.5 |
| 2 | 17.7 | 0.73 | 200 | 39 | 2.8 |
| 3 | 4.43 | 0.37 | 250 | 45 | 2.3 |
| 4 | 17.7 | 0.37 | 230 | 35 | 3.0 |

What is claimed is:

1. A method for the manufacture of a high-expansion type absorbent polymeric powder which forms a non-viscid, gas-permeable gel in the presence of water, comprising:
   (a) partially neutralizing an aqueous solution of an acrylic acid with an alkali hydroxide to obtain at least 75 mol % of an alkali salt of an acrylic acid;
   (b) adding said solution of partially neutralized acid to a suspension of a water-soluble cross-linking agent which is used in an amount of 0.05 to 2% by weight based on said monomer, in an aliphatic hydrocarbon solvent containing a small amount of water and a surfactant;
   (c) partially polymerizing the monomer at at an elevated temperature;
   (d) adding to said partially polymerized mixture a lamellar mineral inorganic substance in an amount of 0.5 to 30% by weight based on said monomer;
   (e) azeotropically distilling away said hydrocarbon and said water; and
   (f) drying the powder thus obtained.

2. A method according to claim 1, wherein said inorganic substance is a binary metal hydroxide possessing an anion-exchange capacity.

3. A method according to claim 2, wherein said binary metal hydroxide possessing an anion-exchange capacity is hydrotalcite.

4. A method according to claim 1, wherein said inorganic substance is a natural or synthetic laminar clay mineral possessing cation-exchange capacity.

5. A method according to claim 1 or 2, wherein said inorganic substance is montmorillonite or montmorillonite treated with an acid.

6. A method according to claim 1, wherein said inorganic substance is talc, pyrophyllite, or kaolinite possessing a lamellar construction.

7. A method according to claim 1, wherein said crosslinking agent is ethylene glycol diglycidyl ether.

8. The method of manufacture according to claim 1 further comprising a monomer which is co-polymerizable with acrylic acids and salts thereof.

* * * * *